United States Patent [19]

Blaeser et al.

[11] Patent Number: 5,490,837
[45] Date of Patent: Feb. 13, 1996

[54] SINGLE OPERATOR EXCHANGE CATHETER HAVING A DISTAL CATHETER SHAFT SECTION

[75] Inventors: David J. Blaeser, Champlin; Jon P. St. Germain, Maple Grove, both of Minn.

[73] Assignee: SciMed Life Systems, Inc., Maple Grove, Minn.

[21] Appl. No.: 204,988

[22] Filed: Mar. 2, 1994

Related U.S. Application Data

[63] Continuation-in-part of Ser. No. 55,695, Apr. 29, 1993, abandoned, which is a continuation-in-part of Ser. No. 725,064, Jul. 5, 1991, Pat. No. 5,281,203, and Ser. No. 843,647, Feb. 28, 1992, abandoned.

[51] Int. Cl.$^6$ .................................................. A61M 29/00
[52] U.S. Cl. ................... 604/96; 604/167; 604/3; 606/194
[58] Field of Search ................... 606/170, 192–197; 604/96–103, 52–53

[56] References Cited

U.S. PATENT DOCUMENTS

| | | | |
|---|---|---|---|
| 3,460,541 | 8/1969 | Doherty | 128/351 |
| 3,707,151 | 12/1972 | Jackson | 128/351 |
| 3,889,686 | 6/1975 | Duturbure | 128/349 |
| 3,890,977 | 6/1975 | Wilson | 128/418 |
| 3,970,089 | 7/1976 | Saice | 128/348 |
| 4,194,513 | 3/1980 | Rhine et al. | 128/750 |
| 4,299,226 | 11/1981 | Banka | 128/344 |
| 4,364,392 | 12/1982 | Strother et al. | 128/325 |
| 4,413,989 | 11/1983 | Schjeldahl et al. | 604/96 |
| 4,423,725 | 1/1984 | Baran et al. | 128/207.15 |
| 4,425,919 | 1/1984 | Alston, Jr. et al. | 128/658 |
| 4,445,892 | 5/1984 | Hussein et al. | 604/101 |
| 4,554,929 | 11/1985 | Samson et al. | 128/772 |
| 4,573,470 | 3/1986 | Samson et al. | 128/344 |
| 4,581,017 | 4/1986 | Sahota | 604/101 |
| 4,606,347 | 8/1986 | Fogarty et al. | 128/344 |
| 4,616,653 | 10/1986 | Samson et al. | 128/344 |
| 4,641,654 | 2/1987 | Samson et al. | 128/344 |
| 4,646,742 | 3/1987 | Packard et al. | 128/344 |
| 4,654,025 | 3/1987 | Cassou et al. | 604/55 |
| 4,655,746 | 4/1987 | Daniels et al. | 604/53 |
| 4,723,550 | 2/1988 | Bales et al. | 128/344 |
| 4,748,982 | 6/1988 | Horzewski et al. | 128/344 |
| 4,762,129 | 8/1988 | Bonzel | 128/344 |
| 4,763,654 | 8/1988 | Jang | 128/344 |
| 4,771,777 | 9/1988 | Horzewski et al. | 128/344 |
| 4,790,315 | 12/1988 | Mueller, jr. et al. | 128/344 |

(List continued on next page.)

FOREIGN PATENT DOCUMENTS

| | | |
|---|---|---|
| 10067/88 | 6/1988 | Australia . |
| 0513818A1 | 5/1992 | European Pat. Off. . |
| WO92/00775 | 1/1992 | WIPO . |
| WO92/13589 | 8/1992 | WIPO . |
| WO93/11826 | 6/1993 | WIPO . |
| WO94/11047 | 5/1994 | WIPO . |

*Primary Examiner*—Stephen C. Pellegrino
*Assistant Examiner*—Nancy Mulcare
*Attorney, Agent, or Firm*—Nawrocki, Rooney & Silvertson

[57] ABSTRACT

An intravascular balloon catheter including a proximal tubular member, preferably a proximal hypotube. The distal end of the proximal hypotube is connected to a transition tube which extends distally. The transition tube has a side port at a point intermediate to which the proximal end of a distal catheter shaft section is connected. The distal catheter shaft section extends distally through an inflatable balloon and forms a lumen extending from the port on the transition tube to the distal end of the catheter for slidably receiving a guide wire therein. The transition tube has a distal end which terminates proximally of the proximal end of the balloon. To provide for fluid communication between the transition tube and the interior of the balloon, inflation holes are provided in the distal catheter shaft section proximal to the distal end of the transition tube and within the balloon. Seals are provided in the distal catheter shaft section proximally of the first set of inflation holes and distally of the second set of inflation holes to allow such lumen to be utilized for both inflating the balloon and passing the guide wire without fluid leakage.

20 Claims, 6 Drawing Sheets

U.S. PATENT DOCUMENTS

| | | | |
|---|---|---|---|
| 4,798,193 | 1/1989 | Giesy et al. | 128/7 |
| 4,798,594 | 1/1989 | Hillstead | 604/167 |
| 4,813,934 | 3/1989 | Engelson et al. | 604/99 |
| 4,817,613 | 4/1989 | Jaraczewski et al. | 128/658 |
| 4,838,268 | 6/1989 | Keith et al. | 128/344 |
| 4,846,174 | 7/1989 | Willard et al. | 128/344 |
| 4,846,193 | 7/1989 | Tremulis et al. | 128/772 |
| 4,848,344 | 7/1989 | Sos et al. | 128/344 |
| 4,877,031 | 10/1989 | Conway et al. | 128/344 |
| 4,892,519 | 1/1990 | Songer et al. | 604/96 |
| 4,898,577 | 2/1990 | Badger et al. | 604/53 |
| 4,906,241 | 3/1990 | Noddin et al. | 606/194 |
| 4,928,693 | 5/1990 | Goodin et al. | 128/637 |
| 4,932,413 | 6/1990 | Shockey et al. | 128/657 |
| 4,932,959 | 6/1990 | Horzewski et al. | 606/194 |
| 4,944,745 | 7/1990 | Sogard et al. | 606/194 |
| 4,964,409 | 10/1990 | Tremulis | 128/657 |
| 4,967,753 | 11/1990 | Haase et al. | 128/662.06 |
| 4,976,720 | 12/1990 | Machold et al. | 606/194 |
| 4,986,814 | 1/1991 | Burney et al. | 604/164 |
| 4,988,356 | 1/1991 | Crittenden et al. | 606/192 |
| 4,994,027 | 2/1991 | Farrell | 604/53 |
| 4,998,917 | 3/1991 | Gaiser et al. | 604/96 |
| 5,003,990 | 4/1991 | Osypka | 128/772 |
| 5,007,901 | 4/1991 | Shields | 604/110 |
| 5,015,231 | 5/1991 | Keith et al. | 604/96 |
| 5,019,042 | 5/1991 | Sahota | 604/101 |
| 5,026,607 | 6/1991 | Kiezulas | 428/423.7 |
| 5,031,636 | 7/1991 | Gambale et al. | 128/772 |
| 5,032,113 | 7/1991 | Burns | 604/96 |
| 5,035,705 | 7/1991 | Burns | 606/194 |
| 5,040,548 | 8/1991 | Yock | 128/898 |
| 5,045,061 | 9/1991 | Seifert et al. | 604/96 |
| 5,046,497 | 9/1991 | Millar | 128/637 |
| 5,047,018 | 9/1991 | Gay et al. | 604/164 |
| 5,047,045 | 9/1991 | Arney et al. | 606/194 |
| 5,057,092 | 10/1991 | Webster, Jr. | 604/282 |
| 5,061,267 | 10/1991 | Zeiher | 606/40 |
| 5,061,273 | 10/1991 | Yock | 606/194 |
| 5,066,285 | 11/1991 | Hillstead | 604/164 |
| 5,078,681 | 1/1992 | Kawashima | 604/53 |
| 5,085,636 | 2/1992 | Burns | 604/99 |
| 5,090,958 | 2/1992 | Sahota | 604/98 |
| 5,114,403 | 5/1992 | Clarke et al. | 604/96 |
| 5,120,308 | 6/1992 | Hess | 604/95 |
| 5,125,905 | 6/1992 | Wright et al. | 604/171 |
| 5,135,494 | 8/1992 | Engelson et al. | 604/99 |
| 5,135,535 | 8/1992 | Kramer | 606/194 |
| 5,141,518 | 8/1992 | Hess et al. | 606/194 |
| 5,147,377 | 9/1992 | Sahota | 606/194 |
| 5,154,725 | 10/1992 | Leopold | 606/194 |
| 5,160,321 | 11/1992 | Sahota | 604/96 |
| 5,171,221 | 12/1992 | Samson | 604/96 |
| 5,171,222 | 12/1992 | Euteneuer et al. | 604/102 |
| 5,171,298 | 12/1992 | Walker et al. | 604/96 |
| 5,180,367 | 1/1993 | Kontos et al. | 604/101 |
| 5,181,921 | 1/1993 | Makita et al. | 606/195 |
| 5,209,728 | 5/1993 | Kraus et al. | 604/96 |
| 5,217,434 | 6/1993 | Arney | 604/99 |
| 5,221,260 | 6/1993 | Burns et al. | 604/99 |
| 5,256,144 | 10/1993 | Kraus et al. | 604/96 |
| 5,290,247 | 3/1994 | Crittenden | 604/171 |
| 5,304,198 | 4/1994 | Samson | 606/194 |
| 5,324,259 | 6/1994 | Taylor et al. | 604/96 |
| 5,348,537 | 9/1994 | Wiesner et al. | 604/96 |
| 5,364,354 | 11/1994 | Walker et al. | 604/96 |

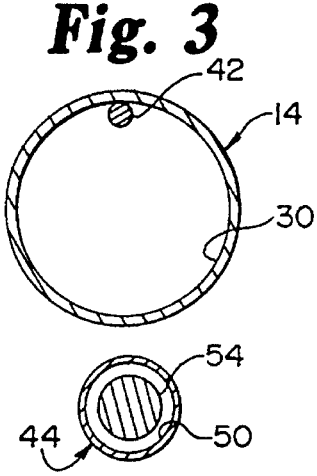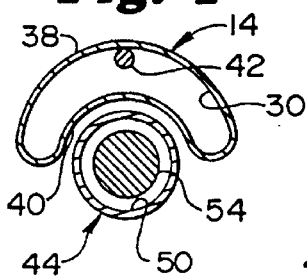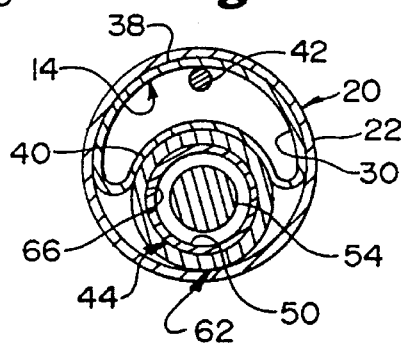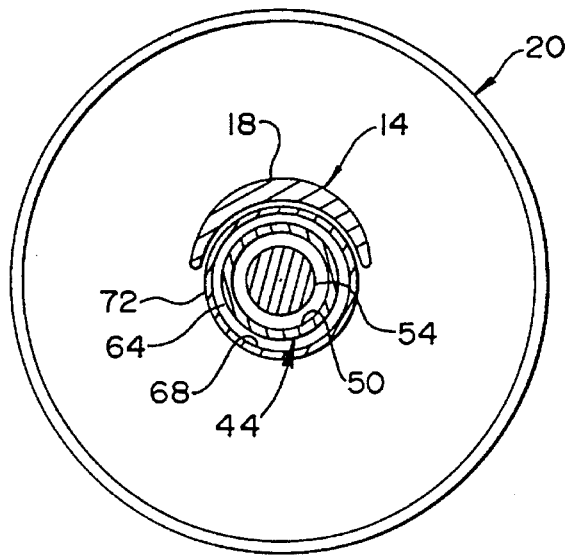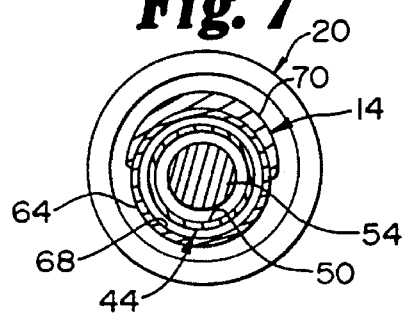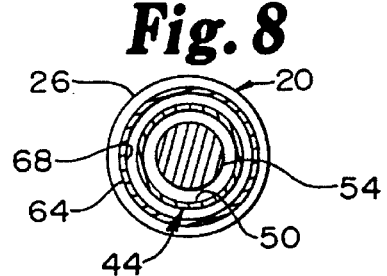

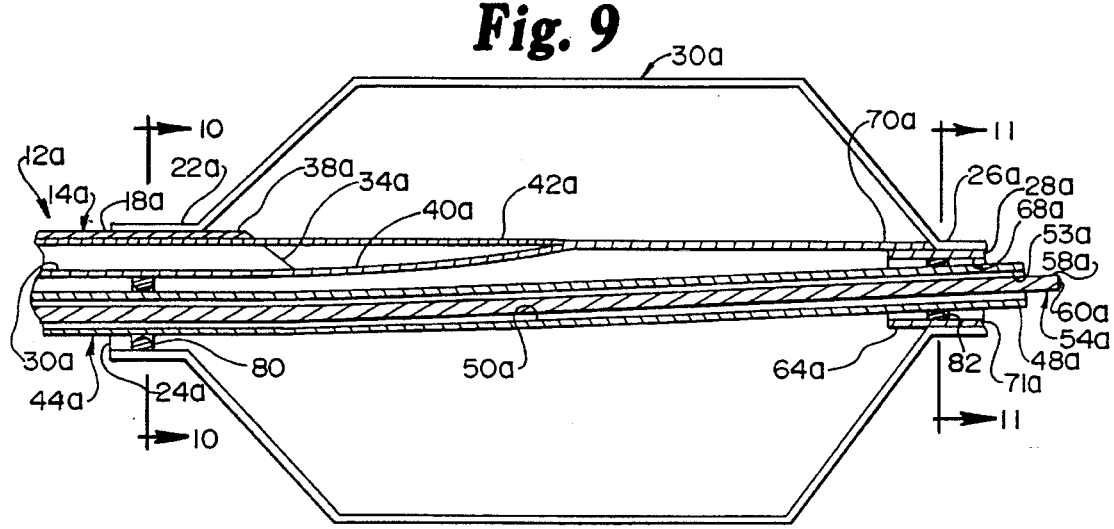
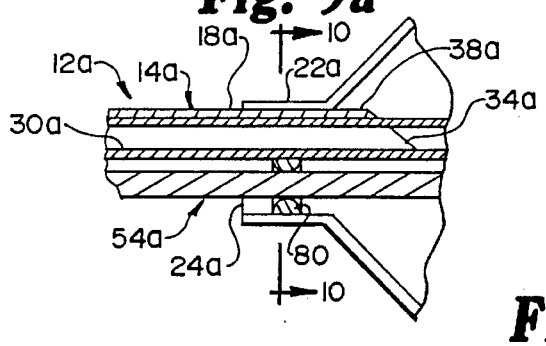
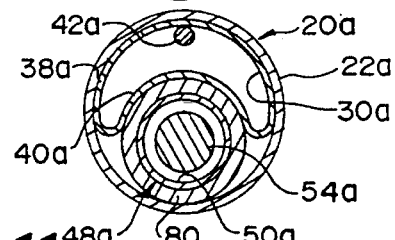
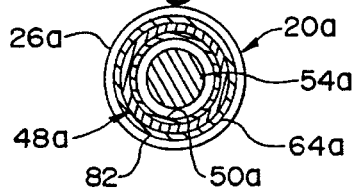
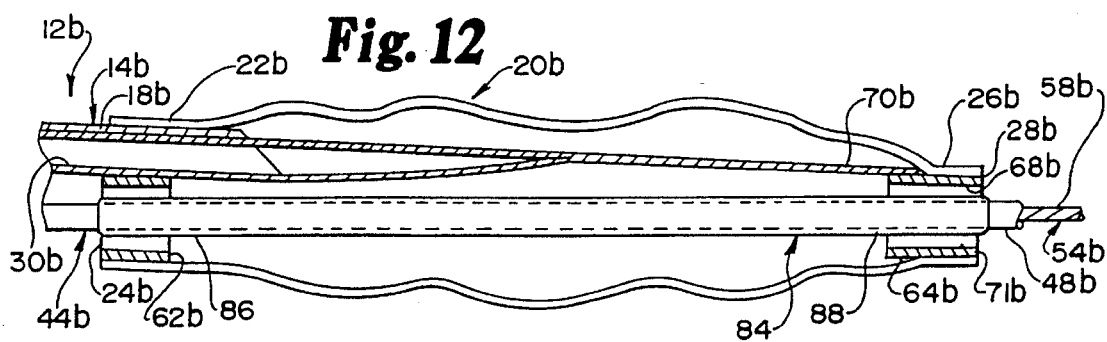

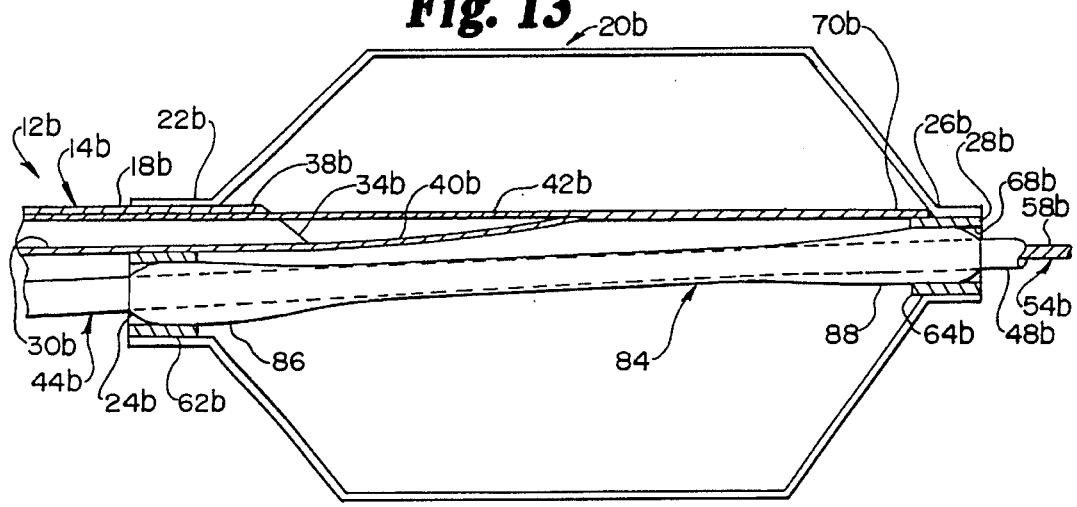
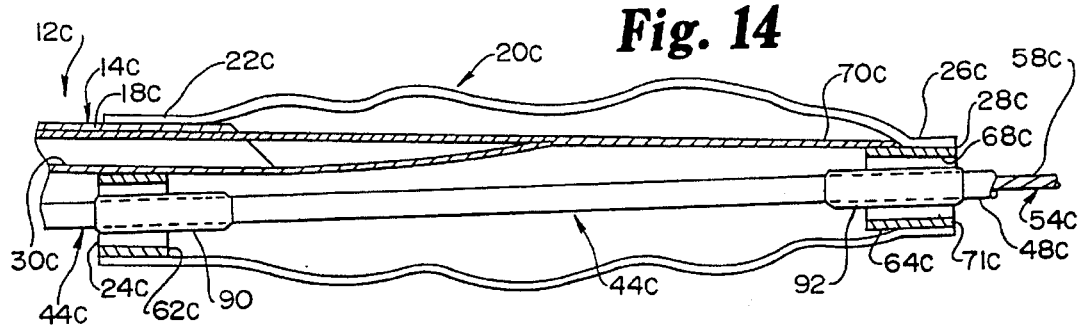
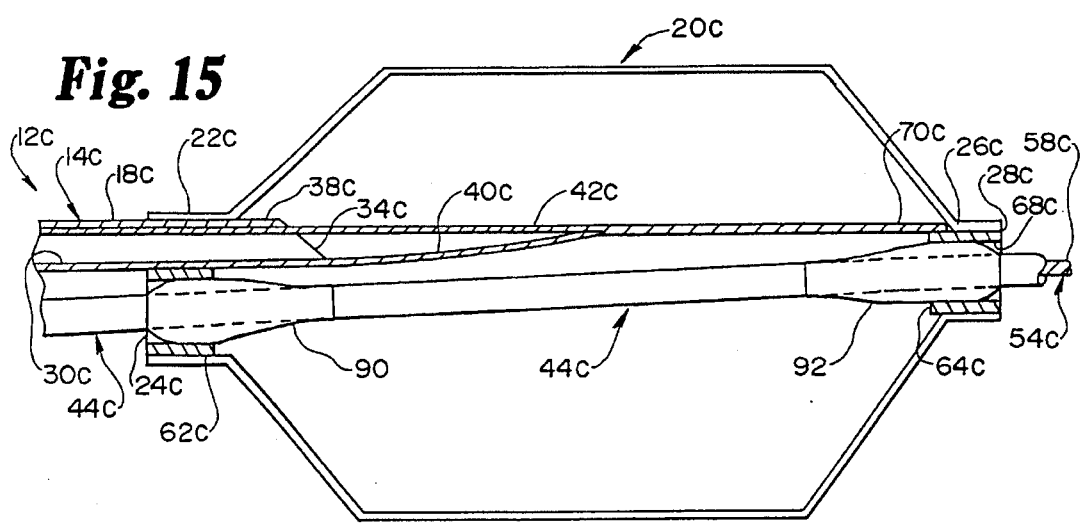

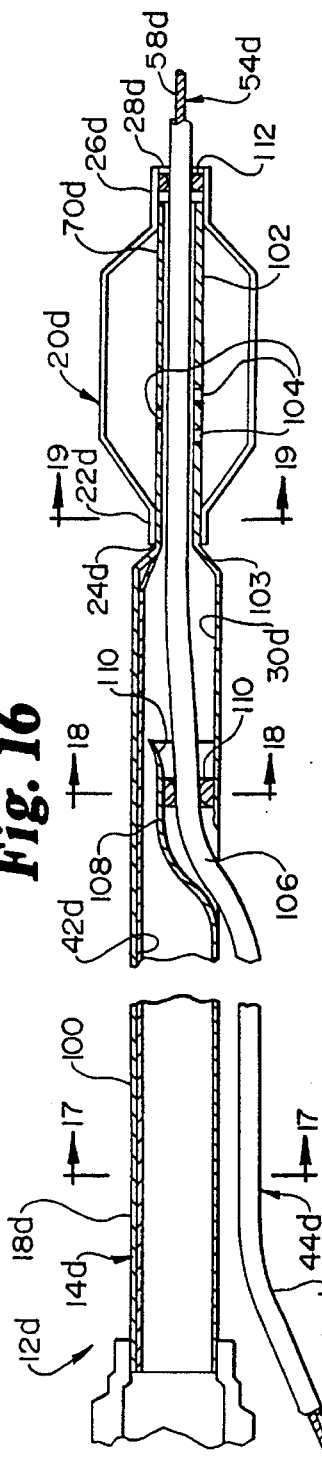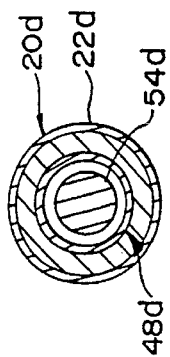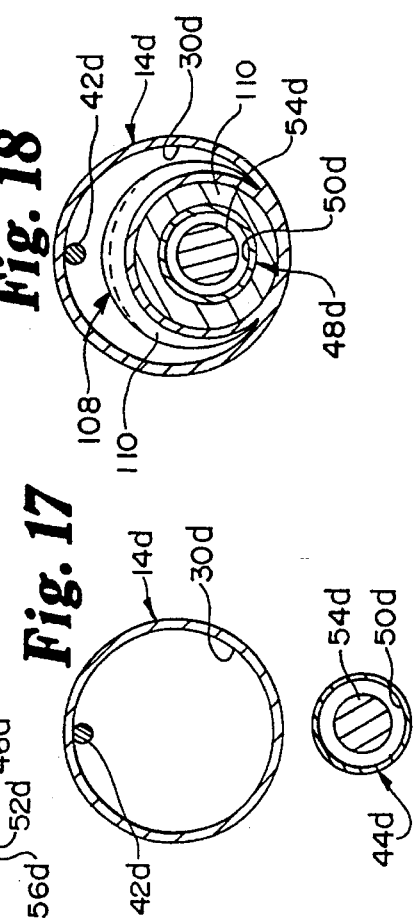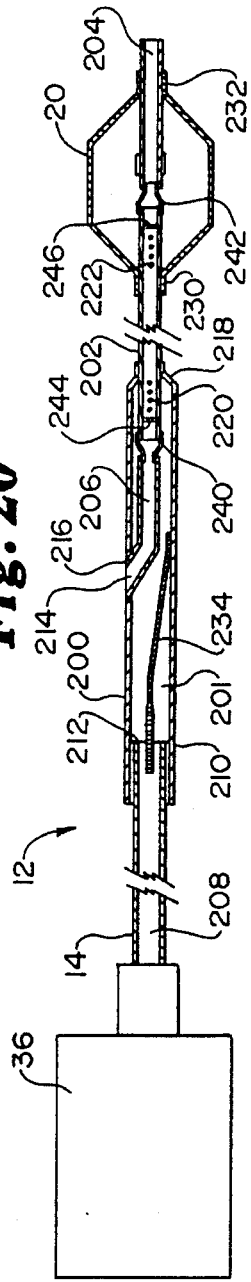

SINGLE OPERATOR EXCHANGE CATHETER HAVING A DISTAL CATHETER SHAFT SECTION

RELATION TO OTHER APPLICATIONS

This application is a continuation-in-part of U.S. patent application Ser. No. 08/055,695, now abandoned, filed Apr. 29, 1993, which is a continuation-in-part of U.S. patent application Ser. No. 07/725,064, now U.S. Pat. No. 5,281,203, filed Jul. 5, 1991, and U.S. patent application Ser. No. 07/843,647, now abandoned, filed Feb. 28, 1992, the entire disclosures of which are specifically incorporated herein by reference.

BACKGROUND OF THE INVENTION

The present invention relates generally to methods and devices used in intravascular therapeutic and diagnostic procedures, and more particularly, to a method and apparatus for performing a balloon angioplasty procedure and for exchanging the components of an intravascular device during the procedure.

Intravascular catheterization devices have proven to be useful and efficient for both therapeutic and diagnostic purposes. Intravascular therapeutic techniques, such as angioplasty, atherectomy, and laser irradiation, have been developed as alternatives to bypass surgery for treating vascular diseases or other conditions that occlude or reduce the lumen size of portions of a patient's vascular system. In particular, balloon angioplasty has proven to be a useful and in many circumstances a preferred treatment for obstructive coronary diseases. Also, intravascular diagnostic techniques, such as ultrasonic imaging and Doppler blood flow measurements, have been developed to measure or image the extent of an occlusion of a vessel (e.g., stenosis). The devices used to perform the aforementioned intravascular therapeutic and diagnostic techniques may be used together or in conjunction with more invasive techniques such as coronary surgery.

These intravascular therapeutic and diagnostic devices have achieved acceptance because of their effectiveness as well as the fact that they can be used in a minor surgical procedure that is relatively nondisruptive to the patient compared to coronary surgery. These devices rely on the positioning of a catheter into the vascular system of a patient via an incision at an accessible location which may be remote from the site of the occlusion or stenosis. For example, the accessible location may be the femoral artery at the groin. The intravascular device is then advanced through the incision via the femoral artery to a desired coronary distal site. The distal sites into which the device may be advanced include the coronary arteries, branch vessels stemming from the external carotid artery such as the occipital and the arteries leading to the vessels of the head and brain, splenic, and the inferior mesenteric and renal arteries leading to the organs of the thorax as well as other vessels.

Because of the small size of some of these vessels and the tortuous passages through the vessels, positioning of a catheter device through a patient's vasculature can be a difficult and time consuming task requiring considerable skill on the part of the physician. For example, in order to perform an angioplasty dilation, the angioplasty balloon catheter must be positioned across the stenosis in the arterial site. The stenosis may be located in a tortuous portion of the coronary vasculature and, furthermore, the obstructive arterial disease may impede crossing the stenosis with the balloon portion of the angioplasty catheter. Thus, not all arterial obstructions can be successfully treated by present intravascular balloon catheter procedures because some arterial obstructions are not readily accessible to a balloon dilation catheter. Accordingly, there is often a need for intravascular catheters of very low profile that can be positioned in narrow, tortuous regions of a person's vasculature.

Another important consideration relating to intravascular procedures, such as angioplasty, relates to the exchange of various devices used to perform the procedures. Intravascular therapeutic and diagnostic devices come in various types and sizes suitable for the vessel size and location in which the treatment is to be performed. Sometimes, it becomes necessary to exchange a first therapeutic device for one of a different size after an unsuccessful attempt has been made to position the first device in the appropriate location. It may also become necessary to exchange therapeutic devices after the first device is successfully positioned in the desired location. This may be necessitated because it becomes apparent that the first device is the wrong size or configuration, or because it is determined that additional therapeutic or diagnostic procedures with a different size or type of device is required.

Several different types of catheter constructions have been developed for positioning intravascular therapeutic or diagnostic catheters through a patient's vasculature. One type of catheter design, commonly referred to as a fixed-wire type catheter, includes a non-removable wire with a tip attached to a distal end of the intravascular catheter. The wire tip facilitates maneuvering the catheter to the desired vessel site. A disadvantage of the fixed-wire type catheter is that if it becomes necessary to exchange a first catheter for a second catheter, the maneuvering procedure must be repeated for the second catheter. As mentioned above, this can sometimes be a tedious and difficult procedure.

Another type of catheter design, referred to as an over-the-wire type catheter, includes a central lumen through the intravascular device that can accommodate a separate guide wire that is movable, .and removable, in relation to the catheter to facilitate positioning the catheter in a remote vessel location over the guide wire. In the over-the-wire construction, the catheter typically includes a lumen adapted to receive the guide wire from a proximal end to the distal end of the device. The guide wire is initially loaded through the lumen of the over-the-wire catheter and extends out from the distal end thereof. Then, the guide wire and the intravascular catheter are advanced together and positioned in the vessel at the desired site. The guide wire may be advanced distally of the distal end of the catheter and steered, as necessary, to traverse tortuous passages of the vessel. The guide wire may then be withdrawn proximally through the lumen of the catheter or may be left in place extending from the distal end of the catheter during the procedure.

The over-the-wire type intravascular catheter facilitates exchanges because a first catheter can be exchanged with a second catheter without removing the guide wire. This allows an exchange of catheters without having to repeat the difficult and time consuming task of positioning the guide wire. In order to leave the distal end of the guide wire in place, it is preferred to maintain a hold on a proximal end portion of the guide wire during the exchange operation. One way to maintain such a hold is to use a guide wire having a sufficiently long length (e.g., 300 cm) so that the entire catheter can be completely withdrawn over the guide wire while maintaining a hold on a portion of the wire. A disadvantage of this method is that the long proximally extending portion of the guide wire may be in the way during the procedure. Another way to maintain a hold on a portion of the guide wire during an exchange operation is to use a guide wire extension. A disadvantage of this method is that not all guide wires are adapted to connect to an extension wire, and moreover, the step of connecting the guide wire to the extension wire can sometimes be tedious and difficult to perform.

A variation of the over-the-wire type catheter which facilitates the exchange of a first catheter with a second catheter is the single-operator exchange type construction. With the single-operator exchange type construction, a guide wire occupies a position adjacent and exterior to the intravascular catheter along proximal and middle portions of the catheter and enters into a short guide wire lumen of the catheter via an opening at a location close to a distal portion of the catheter. With this type of construction, the catheter can be positioned in the patient's vessel by positioning a guide wire in the desired location and advancing the catheter device over the wire. However, in the event it becomes necessary to exchange the catheter, the position of the guide wire can be maintained during withdrawal of the catheter without the use of a long guide wire (e.g., 300 cm) or an extension wire. Because the proximal end of the guide wire is exterior to the proximal end of the catheter, the proximal end of the guide wire can be held during withdrawal of the catheter so that the position of the distal end of the guide wire in the patient's vessel can be maintained. With this type of catheter, it is necessary that the distance from the distal end of the catheter to the proximal guide wire lumen entrance is less than the length of the guide wire that extends proximally out of the catheter.

With known single-operator exchange type constructions, a catheter has at least one lumen extending over substantially the entire length of the catheter and a second guide wire lumen which begins at a location close to a distal portion of the catheter, usually proximal of the balloon and extending distally through the balloon, and opening at the distal end of the balloon. The additional lumen, and associated structure to form such lumen, impact the flexibility of the catheter in its distal region. This also impacts the ability of the catheter to track a guide wire to the site of treatment.

With both fixed wire and over-the-wire type catheters, an introducer sheath and/or a guiding catheter may also be employed. An introducer sheath is used to provide translumenal access to the femoral artery or another appropriate location. Then, with the access provided by the introducer sheath, a guiding catheter may be positioned in the patient's vessel. The guiding catheter may be advanced at least part of the way to the desired site, such as to the aortic arch. The guiding catheter has an internal lumen through which the intravascular device, including the guide wire in an over-the-wire construction, is advanced. One of the functions of the guiding catheter is to support the device. The guiding catheter may be approximately 100 to 106 cm in length. Alternatively, in certain situations, e.g., if positioning of the device does not involve traversing tortuous vessel passages, a guiding catheter may be employed to position an intravascular device without the use of a guide wire.

Just as it is sometimes necessary to exchange an intravascular catheter, it may also become necessary to exchange the guide wire or otherwise assist in advancing the guide wire to the desired location in the vessel. After the guide wire and catheter are in the vessel, it may be determined that the size or shape of the guide wire is inappropriate for advancement to the desired position in a vessel.

For example, the diameter of the guide wire may be too large for advancement past an extensive stenosis or occlusion in a vessel or for advancement in another relatively small vessel. The diameter of the guide wire may also be too small for effective advancement of the guide wire and catheter to the desired location in the vessel. With over-the-wire and single-operator exchange type catheters, the stiffness of a relatively small diameter distal end portion of the guide wire may be insufficient for effective advancement in the vessel. With single-operator exchange type catheters, the proximal portion of the guide wire exterior to the catheter may also lack sufficient stiffness for effective manipulation. Moveover, the transition in profile from a relatively small diameter guide wire and an over-the-wire or single-operator exchange type catheter may cause difficulties when attempting to advance the catheter past an extensive occlusion in the vessel. In contrast to a fixed-wire catheter, these types of catheters typically provide a separate guide wire lumen through at least a portion of the catheter to accommodate the separate guide wire. This element unavoidably increases the overall dimensions of the catheter at least to some degree compared to the fixed-wire catheter. When a smaller diameter guide wire is required for advancement past an extensive stenosis in a vessel, the relatively large transition in profile may make it difficult to subsequently advance the catheter past the stenosis.

It may also be determined that the shape or construction of the guide wire is inappropriate for advancement of the guide wire to the desired position after the guide wire and catheter are in the vessel. For example, a distal portion of the guide wire is often bent a desired amount prior to insertion into the body of a patient to allow manipulation of the guide wire through various vessels. After the guide wire is in a vessel, it may be determined that a guide wire with a different "bend" is necessary to advance further to the desired position in the vessel or to advance into another vessel. The distal tip of the guide wire may also acquire an inappropriate bend during advancement of the guide wire in the vessel. For example, the distal tip of the guide wire may prolapse when movement of the tip is impeded and the guide wire is advanced further in the vessel.

When it is determined that the configuration of the guide wire is inappropriate for advancement in the vessel, the guide wire is typically exchanged for a guide wire having the desired configuration. With an over-the-wire type catheter, the guide wire can be withdrawn through the lumen of the catheter and a second guide wire can be installed while leaving the catheter in position. However, with a single-operator exchange type catheter, a guide wire exchange cannot readily be performed without withdrawing the catheter. Once the distal end of the first guide wire is withdrawn proximally from the proximal guide wire lumen opening of the catheter, a second guide wire cannot readily be positioned in the proximal guide wire lumen opening without also withdrawing the catheter so that the proximal guide wire lumen opening is outside the body of a patient. Although exchanging guide wires is sometimes necessary, it tends to be a difficult and time consuming procedure. Accordingly, there is a need for an improved single-operator exchange type catheter device which provides supplemental assistance for advancing a guide wire to a desired location in a vessel and allows the guide wire to be readily exchanged.

SUMMARY OF THE INVENTION

Briefly stated, the present invention is directed to a method and apparatus for performing a balloon angioplasty procedure and for exchanging intravascular devices during the procedure. The present invention includes a dilation balloon, an elongated shaft and an elongated guide lumen. The shaft has a proximal portion adapted to extend outside the body of a patient and a distal portion adapted for positioning intravascularly during use. The distal portion of the shaft is adapted for connection to the balloon, and an inflation lumen extends through the shaft in fluid flow communication with the balloon. The guide lumen is connected to the catheter such that the guide lumen and catheter are movable relative to each other during use. A proximal portion of the guide lumen is adapted to extend outside the body of a patient and a distal portion is adapted to extend distally of the balloon during use.

Preferably, the guide lumen is in the form of an elongated sleeve member sized and adapted to receive a guide wire. A proximal portion of the guide wire is adapted to extend outside the body of a patient while a distal portion thereof extends out of a distal end of the guide lumen during use. Preferably, the proximal portion of the guide wire extends out of a proximal opening in the guide lumen. In operation, one or both of the guide wire and the catheter shaft can be withdrawn from the guide lumen while the guide lumen remains substantially stationary.

In a preferred embodiment, the entire guide lumen is positioned outside the catheter shaft and a portion thereof is adapted to extend through a portion of a balloon. Alternatively, a portion of the guide lumen is positioned inside a distal portion of the catheter shaft and extends through the balloon.

Also preferably, proximal and distal seal members provide a substantially sealing fit around the guide wire or the guide lumen to inhibit the egress of fluid from the balloon.

In another preferred embodiment of the catheter of the present invention, the catheter shaft comprises a proximal tubular member, a transition tube, and a distal catheter shaft section. The transition tube has a proximal end attached to the distal end of the proximal tubular member and extends distally therefrom. The distal catheter shaft section begins at an opening or port in the wall of the transition tube at a point intermediate and extends distally through the balloon with an opening at the distal end thereof. The distal end of the transition tube terminates a distance proximally from the proximal end of the balloon. The distal catheter shaft section is preferably the only structural element extending from the distal end of the transition tube to the proximal end of the balloon. Through this region, the lumen of the distal catheter shaft section is utilized for both the guide wire and fluid communication of the inflation fluid from the transition tube to the interior of the balloon. Further, the distal catheter shaft section is the only tube which extends through the balloon.

The present invention provides significant advantages over other types of dilation balloon catheters. When it becomes necessary to exchange a first catheter for a second catheter with a more appropriate size or configuration, the catheters can be easily withdrawn and advanced over the guide lumen while holding the guide lumen and guide wire stationary during the exchange. The positioning of the guide lumen outside the catheter shaft and the slidable attachment of the guide lumen to the balloon provides the advantage of a single-operator exchange type construction. Thus, an operator can hold onto a proximal portion of the guide lumen without having to use a relatively long guide lumen or a guide lumen extension. Likewise, the positioning of the guide wire inside the guide lumen with a proximal portion thereof outside a proximal portion of the guide lumen allows an operator to maintain a hold on the guide wire without having to use a relatively long guide wire or a guide wire extension.

The present invention also allows the guide wire to be exchanged when a different size or configuration guide wire is desired. The guide wire can be easily withdrawn through the guide lumen and replaced while the guide lumen and catheter remain in the vessel. Moreover, if it is determined that both the catheter and guide wire need to be exchanged, the catheter can be withdrawn over the guide lumen and the guide wire can be withdrawn through the guide lumen while maintaining a hold on the proximal portion of the guide lumen. A second catheter and guide wire can then be advanced along the guide lumen to the previously attained position.

In addition, the guide lumen facilitates advancement of the guide wire to a desired location in the vessel. For example, the guide lumen provides additional support for manipulating the guide wire in a "bare wire" type procedure in which the guide wire is initially advanced in the vessel prior to insertion of the catheter in the vessel. The guide lumen also provides additional support for the guide wire after the catheter has been inserted in the vessel. For example, the catheter can be advanced to a certain position in the vessel and the guide lumen and guide wire can be advanced further to the desired location in the vessel. In addition, the guide lumen can be used to pre-dilate a stenosis in the vessel before the balloon is inserted into the stenosis. The guide lumen can also be used to straighten a bend in the distal portion of the guide wire.

Another advantage of the present invention is the reduced profile of the balloon when a guide wire is used to guide the catheter in the vessel. The proximal and distal seals provide a seal around the guide wire to prevent fluid from exiting the balloon, thus obviating the need for an inner tube extending through the balloon which tends to increase the profile of the balloon.

Accordingly, the present invention provides a single-operator exchange type apparatus which facilitates ready exchange of a catheter and guide wire and provides supplemental assistance for advancing a guide wire to a desired location in a vessel.

The present invention, together with further objects and advantages, will be best understood by reference to the following detailed description taken in conjunction with the accompanying drawings.

BRIEF DESCRIPTION OF THE DRAWINGS

FIG. 3 is a cross-sectional view of the catheter taken along the line 3—3 in FIG. 1;

FIG. 4 is a cross-sectional view of the catheter taken along the line 4—4 in FIG. 2;

FIG. 5 is a cross-sectional view of the catheter taken along the line 5—5 in FIG. 2;

FIG. 6 is a cross-sectional view of the catheter taken along the line 6—6 of FIG. 2;

FIG. 7 is a cross-sectional view of the catheter taken along the line 7—7 of FIG. 2;

FIG. 8 is a cross-sectional view of the catheter taken along the line 8—8 of FIG. 2;

FIG. 9 is a longitudinal sectional view of a second preferred embodiment of a balloon dilation catheter;

FIG. 9A is a longitudinal sectional view of an alternative embodiment of the catheter shown in FIG. 9;

FIG. 10 is a cross-sectional view of the second preferred embodiment taken along the line 10—10 in FIG. 9;

FIG. 11 is a cross-sectional view of the second preferred embodiment taken along the line 11—11 in FIG. 9;

FIG. 12 is a side view, partially in section, of a third preferred embodiment of a balloon dilation catheter showing a deflated balloon;

FIG. 13 is a side view, partially in section, of the embodiment in FIG. 12 showing an inflated balloon;

FIG. 14 is a side view, partially in section, of a fourth preferred embodiment of a balloon dilation catheter showing a deflated balloon;

FIG. 15 is a side view, partially in section, of the embodiment in FIG. 14 showing an inflated balloon;

FIG. 16 is a side view, partially in section, of a fifth preferred embodiment of a balloon dilatation catheter;

FIG. 17 is a cross-sectional view of the catheter taken along the line 17—17 in FIG. 16;

FIG. 18 is a cross-sectional view of the catheter taken along the line 18—18 in FIG. 16;

FIG. 19 is a cross-sectional view of the catheter taken along the line 19—19 in FIG. 16;

FIG. 20 is a side view, partially in section, of a preferred embodiment of a single-operator exchange catheter having a distal catheter shaft section;

DETAILED DESCRIPTION OF THE PREFERRED EMBODIMENT

The presently preferred embodiments and methodology described herein are applicable to coronary angioplasty procedures and are specifically described in the context of dilation balloon catheters. It should be understood, however, that the embodiments and methodology of the present invention may be adapted for use with other types of intravascular therapeutic devices, such as atherectomy catheters, as well as diagnostic catheters, such as ultrasonic catheters.

Figure 1:
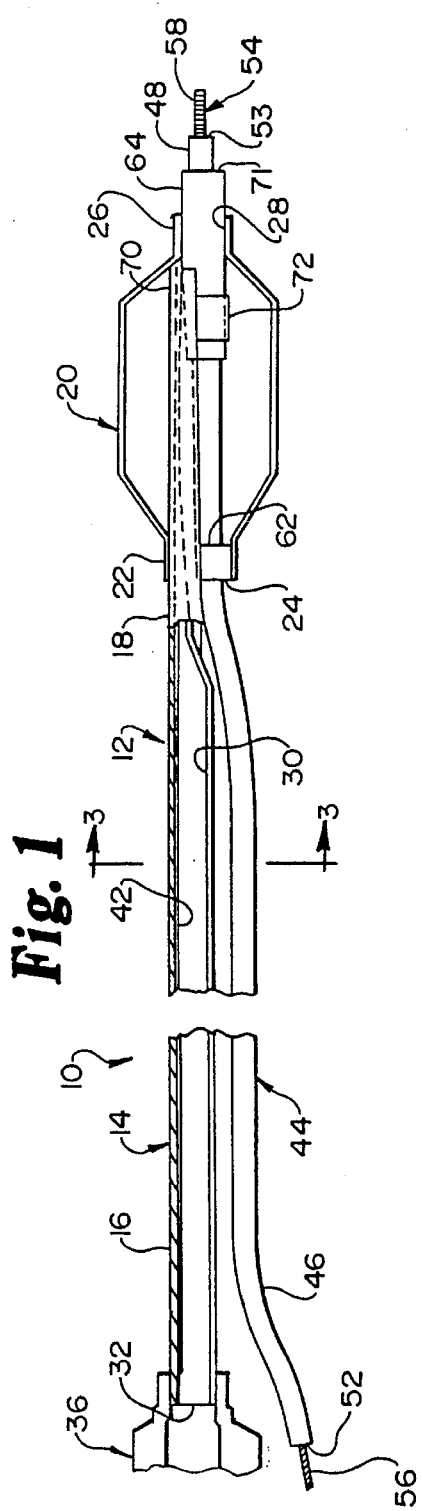
FIG. 1 is a side view, partially in section, of a preferred embodiment of a balloon dilation catheter of the present invention.

Referring to FIG. 1, a first embodiment of a single-operator exchange type intravascular apparatus is indicated generally at 10. The intravascular apparatus 10 includes a balloon dilation catheter 12 having an elongated shaft 14. A proximal portion 16 of the shaft 14 is adapted to extend outside the body of a patient during use, and a distal portion 18 of the shaft 14 is positionable intravascularly during use by manipulation of the proximal portion 16.

A dilation balloon 20 is located at and connected to the distal portion 18 of the catheter shaft 14. The balloon 20 can be formed from a polyolefin copolymer or other polymer material. For example, in one embodiment, the balloon 20 is formed of a polyolefin copolymer (such as that sold by DuPont under the tradename SURLYN as Resin No. 8527) using secondary treatment with 5 to 50 Mega-rad electron beam irradiation to enhance strength in the region of the balloon 20. Preferably, the balloon 20 has a proximal neck portion 22 defining a proximal opening 24, and a distal neck portion 26 defining a distal opening 28. The proximal neck portion 22 preferably has an outer diameter of about 0.040 inches and an inner diameter of about 0.034 inches. The distal neck portion 26 preferably has an outer diameter of about 0.030 inches and an inner diameter of about 0.025 inches.

The distal portion 18 of the shaft 14 extends into the proximal opening 24 in the balloon 20 and is preferably connected to the proximal neck portion 22. The shaft 14 includes an inflation lumen 30 extending therethrough and has a proximal opening 32 and a distal opening 34. A manifold 36 is connected to the proximal portion 16 of the shaft 14 and the dilation balloon 20 is in fluid flow communication with the inflation lumen 30. Inflation fluid is conveyed via the lumen 30 from the manifold 36 to inflate the balloon 20 and therefore dilate a vessel in a conventional manner known in the art. 4

Figure 2:
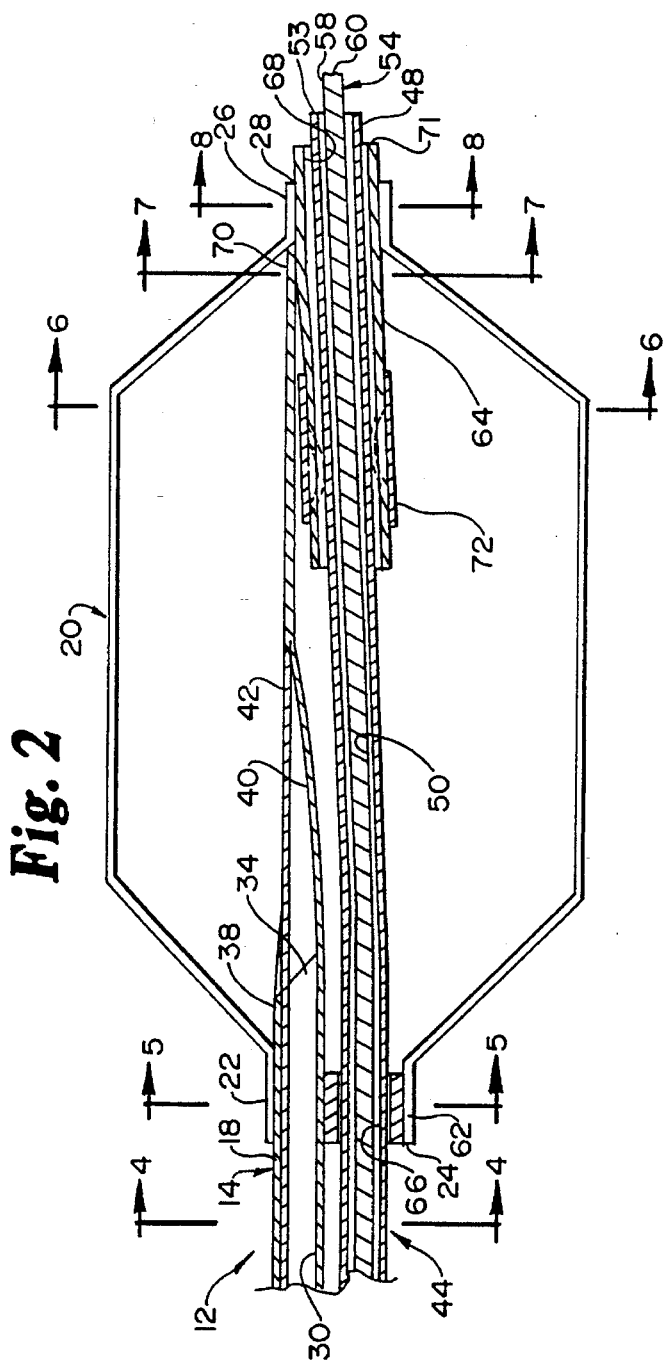
FIG. 2 is a longitudinal sectional view of a distal portion of the catheter shown in FIG. 1.

In a preferred embodiment, the shaft 14 has a length of approximately 135 cm. The proximal portion 16 of the shaft 14 is preferably made of stainless steel hypodermic tubing and the distal portion 18 is made of a relatively flexible polymeric material such as a polyolefin copolymer or polyethylene. This type of shaft is disclosed in U.S. patent application Ser. No. 07/833,099, filed Feb. 10, 1992, the disclosure of which is specifically incorporated herein by reference. In order to minimize the profile of the distal portion 18 of shaft 14, the shape of the shaft 14 and lumen 30 converges from a circular cross-section at the proximal portion 16 thereof (FIG. 3) to a kidney-shaped cross section at the distal portion thereof (FIGS. 4–6). An upper wall 38 and a lower wall 40 of the shaft 14 converge distally of the distal opening 34 in the lumen 30 and extend across the balloon 20 to a position adjacent the distal neck portion 26 of the balloon 20. Preferably, a stiffening wire 42 extends distally from a distal end of the steel tubing and is attached to a distal end of the balloon 20 as disclosed in the '113 patent to provide additional support for the manipulation of the catheter 12. Alternatively, the stiffening wire 42 can be attached to an underside of the upper wall 38 of the shaft and extend to approximately the center of the balloon 20 as shown in FIGS. 1 and 2.

To facilitate the operation and exchange of the components of the intravascular apparatus 10, an elongated guide lumen 44 is adapted to extend through the proximal and distal openings 24 and 28 of the balloon 20 for slidable movement relative to the balloon 20 during use. The guide lumen 44 also has an inner chamber 50 extending therethrough from a proximal end 52 to a distal end 53 thereof for slidably receiving a conventional guide wire 54. The guide lumen 44 has a sufficient length, preferably about 135 cm, so that a proximal portion 46 of the guide lumen 44 can extend outside the body of a patient during use while a distal portion 48 extends distally of the balloon 20. Preferably, the guide lumen 44 is approximately the same length as a conventional catheter.

The guide lumen 44 may also be provided in different sizes to accommodate different size devices. For example, the guide lumen 44 can be provided with an inner diameter of 0.017 inches and an outer diameter of 0.020 inches for use with a 0.014 inch guide wire. For use with a 0.010 inch guide wire, the guide lumen 44 may be provided with an inner diameter of 0.013 inches and an outer diameter of 0.016 inches.

Preferably, the guide lumen 44 is made of a polymeric material, such as polyimide, and has a low friction coating, such as Teflon®, on both the inner and outer surfaces thereof. A coating on the inner surface enhances guide wire movement through the chamber 50, and a coating on the outer surface enhances movement of the guide lumen 44 through a guiding catheter, a vessel, or the balloon 20. Alternatively, the guide lumen 44 can be made of other materials, such as polyurethane, polyester, or other polymers. The guide lumen 44 can also be made of a polyimide-teflon composite material, or reinforced with wire or a braid of metal or plastic or other materials.

To provide greater stiffness at the proximal portion 46 of the guide lumen 44 compared to the distal portion 48, the pitch of a wound reinforcing wire can be varied a desired amount along the length of the guide lumen 44. The variable pitch wire can provide increased stiffness at the proximal portion 46 of the guide lumen 44 to facilitate manipulation of the entire guide lumen 44. The variable pitch wire can also provide sufficient flexibility at the distal portion 48 of the guide lumen 44 to allow the guide lumen 44 to easily follow the guide wire 54 through a vessel. Also alternatively, the coatings may be made of other materials such as a hydrophilic or silicone coating. In addition to or instead of the low friction coating, a metallic or foil coating may also be incorporated on the inner or outer surface of the guide lumen 44.

The guide wire 54 has a sufficient length, preferably about 160–190 cm, so that a proximal portion 56 of the guide wire 54 can extend outside the body of a patient from an opening in the proximal end 52 in the guide lumen 44 while a distal portion 58 extends distally from an opening in the distal end 53 of the guide lumen 44. The proximal portion 56 of the guide wire 54 can also extend out of an opening in the guide lumen located distally of the proximal end 52 of the guide lumen 44. In addition, the guide wire 54 can have an outer diameter between 0.008 and 0.022 inches, although conventional guide wires typically have a diameter of 0.010, 0.014 or 0.018 inches.

In a first embodiment, a proximal seal member 62 is sealingly connected to the proximal neck portion 22 of the balloon 20 and a distal seal member 64 is sealingly connected to the distal neck portion 26 of the balloon 20. The proximal and distal seal members 62 and 64 have passageways 66 and 68 therethrough for slidably receiving the guide lumen 44. The seal members 62 and 64 are preferably configured as collars and are made of a polymeric material, such as polyimide, polyurethane, polyester or the like. An upper portion of the proximal seal member 62 is attached to the curved bottom wall 40 of the catheter shaft 14, and a lower portion is attached to the proximal neck portion 22 of the balloon 20. The entire periphery of the distal seal member 64 is attached to the distal neck portion 26, and a distal end 70 of the shaft 14 is attached to a top portion of the distal seal member 64 proximally of the neck portion 26. In use, the distal portion 48 of the guide lumen 44 is adapted to extend distally from an end 71 of the distal seal member 64 while the proximal portion 46 is outside the body of a patient. Preferably, the outer diameter of the guide lumen 44 is only slightly smaller than the inner diameters of the proximal and distal seal members 62 and 64 to create a tolerance fit which allows slidable movement of the guide lumen 44 through the seal member passageways 66 and 68. When the balloon 20 is inflated with fluid, the tolerance fit between the guide lumen 44 and the proximal and distal seal members 62 and 64 inhibits inflation fluid from exiting the balloon 20.

In addition, the distal seal member 64 preferably extends proximally into the balloon 20 and has an expandable, tubular valve member 72 made of an elastomeric material such as TECOTHANE or the like. As shown in dashed lines in FIG. 2, the valve member 72 expands radially inward against the guide lumen 44 when the balloon 20 is inflated to further seal any space between the guide lumen 44 and the distal seal member 64. A valve member of similar construction can also be incorporated into the proximal seal member 62 if desired.

FIGS. 9–19 illustrate alternative embodiments of the present invention. Since these embodiments are similar to the previously described embodiment, similar parts appearing in FIGS. 9–15 are represented by the same, corresponding reference numeral, except for the corresponding letter in the numerals of the latter.

In the embodiment shown in FIGS. 9–11, a pair of split O-ring type seals are provided to prevent inflation fluid from exiting the balloon 20a. An upper portion of a proximal split O-ring 80 is attached to the curved bottom wall 40a of the catheter shaft 14a, and a lower portion is attached to the proximal neck portion 22a of the balloon 20a. The entire periphery of a distal O-ring 82 can be attached to the distal seal member 64a as shown in FIG. 9 or bonded directly to the distal neck portion 26a of the balloon 20. The split O-rings 80 and 82 are preferably made of a relatively soft durometer urethane material or the like and can be preformed or molded into the balloon 20a.

In a molding operation, a polyurethane adhesive or the like can be injected into a shaped mold temporarily positioned in the neck portion of the balloon 20a. Although the contact surfaces of the O-rings 80 and 82 are shown as rounded surfaces, the O-rings can be formed in any desired shape to facilitate slidable movement of the guide lumen 44a while providing an effective seal when the balloon 20a is inflated. The shape and material of the O-ring allows greater deformation as a result of pressure from the inflation fluid, which may provide a more effective seal. Moreover, the "single point" contact of the proximal and distal O-rings 80 and 82 with the guide lumen 44a may facilitate advancement and withdrawal of the catheter 12a over the guide lumen 44a because the decreased contact area tends to reduce frictional forces acting on the guide lumen 44a.

In the embodiment shown in FIGS. 12–13, the guide lumen 44b is configured with an enclosed, deformable bladder-type sheath 84 surrounding a portion thereof. The sheath 84 has a constant volume of fluid therein (not shown) and is approximately the same length as the distance between the proximal and distal seal members 62b and 64b of the balloon 20b. Prior to inflation of the balloon 20b, the guide lumen 44b is advanced or withdrawn until proximal and distal end portions 86 and 88 of the sheath 84 are substantially aligned with the proximal and distal seal members 62b and 64b (FIG. 12). When the balloon 20b is inflated with fluid, the fluid in the sheath 84 is displaced outwardly toward the end portions 86 and 88 (FIG. 13). As a result, the volume of space occupied by the end portions 86 and 88 increases such that the end portions bear against the seal members 62b and 64b to create an effective seal which prevents the inflation fluid from exiting the balloon 20b.

Alternatively, the sheath 84b can be provided in the form of spaced apart proximal and distal sheaths 90 and 92 surrounding the guide lumen 44c as shown in FIGS. 14 and 15. The distance between the sheaths 90 and 92 is approximately the same as the distance between the seal members 62c and 64c. The sheaths 90 and 92 are aligned with the corresponding seal members 62c and 64c prior to inflation of the balloon 20c (FIG. 14), and the inflation fluid displaces the fluid in the sheaths 90 and 92 outwardly to create a seal between the sheaths 90 and 92 and the corresponding seal members 62c and 64c. In either of the embodiments shown in FIGS. 12–15, the seal members can be eliminated and the sheaths can be configured to bear directly against the corresponding neck portions of the balloon when displaced by the inflation fluid.

Alternatively, a bladder-type valve member which surrounds the guide lumen 44 and expands when filled with fluid can provide an active seal. Valve members of this type are disclosed in U.S. Pat. No. 5,085,636, issued Feb. 4, 1992, the disclosure of which is specifically incorporated herein by reference. Such a seal could be activated by the inflation fluid which fills the balloon 20 or by a separate flow of fluid through a micro-tube connected to the bladder.

In any of the embodiments described herein, the proximal and distal seal members can be configured to slidably receive and provide an effective seal around a guide wire without the use of a guide lumen (see, e.g., FIG. 9A). One advantage of this configuration may be the reduced profile of the balloon 20 resulting from the elimination of an inner tube inside the balloon 20. Such a configuration may also facilitate the flow of a radiopaque dye solution which is typically introduced into the vessel after an angioplasty procedure to determine whether an acceptable blood flow has been established through the vessel. When a 0.014 inch guide wire is used, the proximal neck portion 22 preferably has an outer diameter of about 0.036 inches and an inner diameter of about 0.030 inches. The distal neck portion 26 preferably has an outer diameter of about 0.025 inches and an inner diameter of about 0.020 inches. Thus, the distal and proximal seals inhibit fluid from exiting the balloon 20 without separating the movable guide wire from the inflation fluid in the balloon.

FIGS. 16–19 illustrate yet another embodiment of the present invention. In this embodiment, the shaft 14d has a relatively large diameter body portion 100 and a smaller diameter distal end portion 102 which extends through the proximal and distal openings 24d and 28d in the balloon 20d. Preferably, the juncture of the body portion 100 and the distal end portion 102 is defined by a tapered shoulder 103 adjacent the balloon 20d. The distal end portion 102 of shaft 14d is sealingly attached to the proximal and distal neck portions 22d and 26d of the balloon 20d. The balloon 20d is inflated by conveying fluid via the inflation lumen 30d of the shaft 14d through a plurality of openings 104 formed in the distal end portion 102 of the shaft. Instead of slidably attaching the guide lumen 44d to the balloon 20d and positioning the entire guide lumen 44d outside the shaft 14d, a portion of the guide lumen 44d is movably positioned within a distal portion of the inflation lumen 30d of shaft 14d. Because the guide lumen 44d is positioned within the reduced diameter shaft lumen 30d rather than outside the shaft 14d, the profile of catheter 12d is minimized to allow insertion into relatively small vessels. The constant outer diameter of the distal end portion 102 of the shaft 14d also may provide a better joint between the balloon 20d and the shaft 14d.

An opening 106 is provided in the body portion 100 of the shaft 14d, preferably about 10–30 cm proximally from the balloon 20d, for receiving the guide lumen 44d. The guide lumen 44d is guided by an inner core 108 which extends distally a relatively short distance, preferably about 5–15 mm, into the inflation lumen 30d from the opening 106. An end portion 110 of the core 108 is flared to direct the guide lumen 44d into the core 108 when the guide lumen 44d is inserted in a proximal direction through the distal end portion 102 of the shaft 14d. To prevent fluid from exiting through the core 108 and out the opening 106, a seal member 110 is sealingly connected to the core 108. The seal member 110 is preferably a split O-ring type seal which is described in more detail above. A split O-ring type seal member 112 can also be provided in the distal neck portion 26d for sealingly engaging the guide lumen 44d.

Alternatively, the opening 106 and core 108 of the shaft 14d, along with the seal members 110 and 112, can be configured to slidably receive a guide wire or other intravascular device without the use of the guide lumen 44d. The elimination of the guide lumen would allow the shaft to be configured with a smaller outer diameter, thus reducing the profile of the catheter.

Another preferred embodiment of a single-operator exchange catheter of the present invention is depicted in FIGS. 20–23. With this embodiment, the catheter 12 includes a proximal tubular member 14, a transition tube 200, and a distal catheter shaft section 202. The distal catheter shaft section 202 is preferably the only tubular member extending distally beyond the distal end of the transition tube 200 through the balloon 20 with a distal opening 204 at the distal end of the catheter 12. By the use of active and/or passive seals and the configuration described below, the distal catheter shaft section 202 provides a lumen 206 for both slidably receiving the guide wire 54 (whether incorporating a guide lumen or guide wire only) and for providing fluid communication for inflation fluid from the distal area of the transition tube 200 to the inside of balloon 20.

The proximal tubular member 14 includes at least one tubular section and has a lumen 208 extending therethrough. The proximal tubular member 14, as with the embodiments described above, extends distally from a manifold 36. The proximal tubular member 14 is preferably a stainless steel hypotube. As shown in FIG. 20, the transition tube 200 preferably has a proximal end 210 connected proximate to the distal end 212 of the proximal tubular member 14. The transition tube 200 has a lumen 201 in fluid communication with the lumen 208 of the proximal tubular member 14. The transition tube 200 further includes a radial port 214. The radial port 214 is created by boring a hole or otherwise forming a passage through the side wall of the transition tube 200. Although not preferable, the proximal tubular member 14 and transition tube 200 could be a single tubular member or main tubular member and thus the radial port 214 would be through the side wall of the main tubular member 14.

Figure 21:
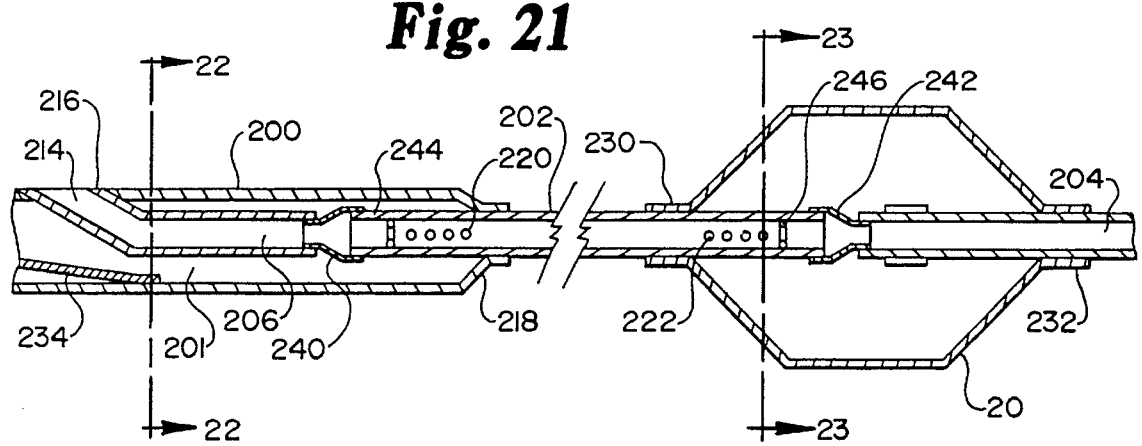
FIG. 21 is a longitudinal sectional view of a distal portion of the catheter shown in FIG. 20.
Figure 22:
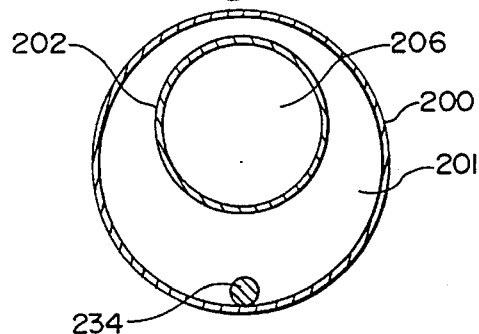
FIG. 22 is a cross-sectional view along line 22—22 of FIG. 21.
Figure 23:
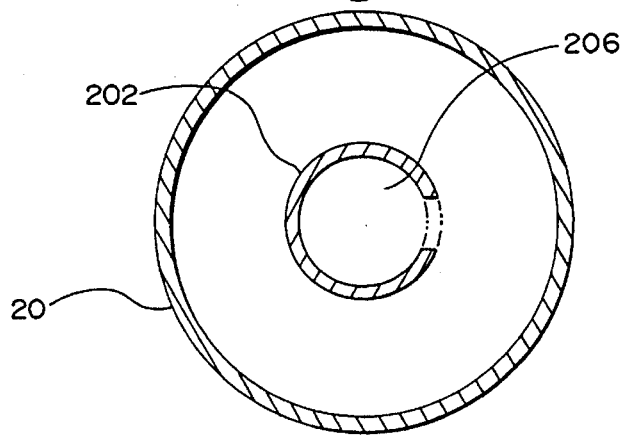
FIG. 23 is a cross-sectional view along line 23—23 of FIG. 21.

The distal catheter shaft section 202, as best depicted in FIG. 21, has a proximal end 216 connected to the radial port 214. A lumen 206 extends through the distal catheter shaft section 202 and extends distally beyond the distal end 218 of the transition tube 200 to the distal end 204 of the catheter 12.

The distal end 218 of the transition tube 200 is sealingly connected to the outside surface of the distal catheter shaft section 202. The transition tube 200 and distal catheter shaft section 202 are preferably manufactured from a polymer such as polyethylene. Bonds between these polymeric tubular members are preferably accomplished through thermal welding, however it is recognized that adhesives may also be utilized as described for previous embodiments.

The distal catheter shaft section 202 further includes at least one first inflation hole 220 which extends through the wall thereof intermediate between the radial port 214 and the distal end 218 of the transition tube 200.

The balloon 20 has a proximal end 230 and a distal end 232 sealingly connected to the distal catheter shaft section 202 at a location spaced distally from the distal end 218 of the transition tube 200. The distal catheter shaft section 202 further includes at least one second inflation hole 222 through the wall thereof intermediate the ends of the balloon 230, 232.

With the above structure, the lumen 201 of the transition tube 200 is in fluid communication with the interior of the balloon 20 through the first inflation hole 220, a portion of the lumen 206 of the distal catheter shaft section 202 and the second inflation hole 222.

A core member 234 can be disposed within the lumens 208, 201 of the proximal tubular member 14 and the transition tube 200 over at least a portion of their lengths. The core member 234 is preferably a stainless steel wire. In one embodiment, the core member 234 extends from proximate the distal end 212 of the proximal tubular member 14 distally to a point proximate the radial port 214.

Because a single tubular member, namely the distal catheter shaft section 202, eliminates the need for a separate guide wire lumen and inflation lumen from a point proximal to the balloon through the balloon, the profile of a catheter designed in accordance with this embodiment is smaller and allows for better access to smaller vessels and better flow of fluid around the catheter 12, such as blood or radiopaque contrast fluid. To prevent leakage of inflation fluid proximal to the first inflation hole 220 and distal to the second inflation hole 222, means for sealing around the guide wire disposed within the lumen 206 of the distal catheter shaft section 202 are provided. As with previous embodiments, many combinations of seals are possible.

In one embodiment, depicted in FIGS. 20–23, a first 240 and a second 242 active seal means are provided for limiting the egress of inflation fluid. The first active seal means 240 is disposed within the lumen 206 of the distal catheter shaft section 202 between the radial port 214 and the first inflation hole 220. This seal prevents or reduces leakage of inflation fluid out the port 214. The second active seal means 242 is disposed within the lumen 206 of the distal catheter shaft section 202 between the distal end 204 of the catheter and the second inflation hole 222. This seal prevents or reduces leakage out the distal end of the catheter. The active seal means 240, 242 are preferably sections of flexible tubing extending across a gap in the length of the distal catheter shaft section 202. A preferable material of construction is and elastomeric material such as TECOTHANE or PEBA.

In an alternative embodiment, the first 240 and second 242 active seal means could incorporate an elastomeric material which extends across a gap in the length of the distal catheter shaft section 202 and be connected to the inside surface of the distal catheter shaft section 202. With this design, a pressure permeable, longitudinally stiff member can be extended over the gap and affixed to the outside surface of the distal catheter shaft on each side of the gap. The pressure permeable, longitudinally stiff member can provide additional stiffness in the region of the active seals which can assist pushability of the catheter 12.

First and second passive seal means 244, 246 can also be included, as depicted in FIGS. 20–21. The passive seals assist the active seals in preventing or reducing the egress of inflation fluid. The first passive seal means 244 is disposed within the lumen 206 of the distal catheter shaft section 202 between the radial port 214 and the first inflation hole 220. The second passive seal 246 is also disposed within the lumen 206 of the distal catheter shaft section 202, however, between the distal end 204 of the catheter 12 and the second inflation hole 222. The passive seal means are preferably O-ring seals manufactured from a polymeric material such as polyurethane resin. Other manufacturing molding materials and methods may be utilized.

In operation of the intravascular apparatus 10, intravascular access is initially made in a conventional manner. If the procedure is a percutaneous translumenal angioplasty (PCTA) procedure, access is made via the femoral artery. A conventional introducer and guiding catheter (not shown) can be employed in a manner that is well known in the art. When used with the described embodiments of the present invention, a guiding catheter should have a lumen of sufficient size to accommodate the catheter 12, guide lumen 44 and guide wire 54.

To initially position the intravascular apparatus 10 in a patient's vessel, the guide wire 54 is preferably inserted into the guide lumen 44 while the entire guide lumen is outside the body such that the distal tip portion 58 of the guide wire 54 extends beyond the guide lumen 44. The combination of the guide wire 54 and guide lumen 44 is then advanced to a desired location in a vessel, and the catheter 12 is advanced over the guide lumen 44. The guide wire 54 can be inserted into the vessel prior to advancement of the guide lumen 44 over the guide wire, or the guide lumen 44 can be inserted into the vessel prior to advancement of the guide wire 54 through the guide lumen 44. If the catheter 12 is configured to receive the guide wire 54 without the guide lumen 44, the guide wire 54 can be advanced to a desired location in a vessel in a "bare wire" technique and the catheter 12 can be passed over the guide wire 54.

Preferably, the combination guide wire 54 and guide lumen 44 are advanced until the distal portions 48 and 58 thereof reach a distal end of the guiding catheter. The guide wire 54 may be further advanced in the vessel alone, or the guide lumen 44 may be advanced along with the guide wire 54. Thus, the distal portion 48 of the guide lumen 44 can provide additional support for the distal portion 58 of the guide wire 54 when desired. For example, when the guide wire 54 is initially advanced alone, it may become difficult at some point to further advance the guide wire because it does not have sufficient stiffness for effective manipulation. The guide lumen 44 can then be advanced to support the guide wire 54 and assist its advancement in the vessel. Thus, using the guide lumen 44 may avoid having to exchange the guide wire 54 for another guide wire having a larger diameter. If an exchange is required because the size or configuration of the guide wire 54 is inappropriate for further advancement in the vessel, the guide lumen 44 is advanced until the distal end 53 reaches a distal end 60 of the guide wire 54. The guide wire 54 is withdrawn from the guide lumen 44, and a desired bend can be formed in the distal portion 58 of the guide wire 54 or another guide wire can be obtained. The newly configured guide wire is then advanced through the guide lumen 44 to the previously attained position.

The guide lumen 44 can also be used to straighten a bend in the distal portion 58 of the guide wire 54 while inside a vessel. As noted above, the distal portion 58 of the guide wire 54 is often bent a desired amount prior to insertion into the body of a patient to allow manipulation of the guide wire 54 through various vessels. The distal portion 58 of the guide wire 54 may also bend as a result of advancement of the guide wire 54 when movement of the distal tip is impeded in the vessel. If the bend is inappropriate for further advancement of the guide wire 54 to the desired location in the vessel or for advancement into a different vessel, the guide lumen 44 can be advanced over the guide wire 54 to straighten the distal portion 58 a desired amount. In addition, the guide lumen 44 can be advanced over the guide wire 54 after the guide wire is advanced past a stenosis in the vessel to pre-dilate the stenosis before insertion of the balloon 20. The guide wire 54 can also be moved within the guide lumen 44 when the balloon 20 is inflated inside a vessel.

As best shown in FIG. 1, a substantial portion of the guide lumen 44 and guide wire 54 is positioned outside the catheter shaft 14 to allow a single-operator exchange of the catheter 12 for a second catheter. When a different size or configuration catheter is required, the catheter 12 is withdrawn so that the balloon 20 passes over the guide lumen 44 while an operator maintains a hold on the proximal portion 46 of the guide lumen 44 and the proximal portion 56 of the guide wire 54. The balloon of a second catheter can then be advanced over the guide lumen 44 to position the second catheter in the same location previously attained by the first balloon catheter 12. This single-operator exchange type configuration allows the operator to maintain a hold on the guide lumen 44 and guide wire 54 without using an extension or a relatively long guide lumen and guide wire.

The guide lumen 44 therefore provides for the independent or substantially contemporaneous exchange of the guide wire 54 and the catheter 12. When an exchange of the guide wire 54 is required, the guide wire 54 is withdrawn through the guide lumen 44 and replaced with a second guide wire. Thus, the guide wire 54 can be exchanged before the catheter 12 has been inserted in the vessel, while the catheter 12 remains in the vessel, or after the catheter 12 has been withdrawn. Likewise, the catheter 12 can be exchanged while the guide wire 54 remains in the vessel or after the guide wire 54 has been withdrawn. In either procedure, the position of the guide lumen 44 is maintained in the vessel by holding onto the proximal portion 46 of the guide lumen.

Thus, a single-operator exchange type intravascular apparatus is provided which facilitates ready exchange of a catheter and guide wire and provides supplemental assistance for advancing a guide wire to a desired location in a vessel.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the following claims, including all equivalents thereof, which are intended to define the scope of the invention.

What is claimed is:

1. An intravascular catheter assembly comprising:
   (a) a main tubular member including at least one tubular section, said member having a lumen extending therethrough and a radial port intermediate the length thereof;
   (b) a distal catheter shaft section having a proximal end connected to said radial port and a lumen therethrough, said distal catheter shaft section extending distally beyond the distal end of said proximal tubular member, wherein said distal end of said proximal tubular member is sealingly connected to said distal catheter shaft section, said distal catheter shaft section further having at least one first inflation hole through the wall thereof intermediate between said radial port and said distal end of said proximal tubular member; and,
   (c) a balloon having a proximal end and a distal end sealingly connected to said distal catheter shaft section at a location spaced distally from the distal end of said proximal tubular member, said distal catheter shaft section having at least one second inflation hole through the wall thereof intermediate the ends of said balloon, such that said lumen of said proximal tubular member is in fluid communication with said balloon through said first inflation hole, said lumen of said distal catheter shaft section and said second inflation hole.

2. The intravascular catheter assembly of claim 1, further comprising a core member disposed within said lumen of said proximal tubular member over at least a portion of the length thereof.

3. The intravascular catheter assembly of claim 1, further comprising a first and a second active seal means for limiting the egress of inflation fluid, said first active seal means disposed within said lumen of said distal catheter shaft section between said radial port and said first inflation hole and said second active seal means disposed within said lumen of said distal catheter shaft section between the distal end thereof and said second inflation hole.

4. The intravascular catheter assembly of claim 3, wherein each of said active seal means includes a section of flexible tubing extending across a gap in the length of said distal catheter shaft section.

5. The intravascular catheter assembly of claim 4, wherein said flexible tubing is manufactured from an elastomeric material.

6. The intravascular catheter assembly of claim 1, further comprising a first and a second passive seal means for limiting the egress of inflation fluid, said first passive seal means disposed within said lumen of said distal catheter shaft section between said radial port and said first inflation hole and said second passive seal means disposed within said lumen of said distal catheter shaft section between the distal end thereof and said second inflation hole.

7. The intravascular catheter assembly of claim 6, wherein said passive seal means include o-rings.

8. An intravascular catheter assembly comprising:
   (a) a proximal tubular member having a lumen extending therethrough;
   (b) a transition tube having a proximal end connected to and extending distally from the distal end of said proximal tubular member and having a lumen in fluid communication with said lumen of said proximal tubular member, said transition tube further having a radial port intermediate the length thereof;
   (c) a distal catheter shaft section having a proximal end connected to said radial port and a lumen therethrough, said distal catheter shaft section extending distally beyond the distal end of said transition tube, wherein said distal end of said transition tube is sealingly connected to said distal catheter shaft section, said distal catheter shaft section further having at least one first inflation hole through the wall thereof intermediate between said radial port and said distal end of said transition tube; and,
   (d) a balloon having a proximal end and a distal end sealingly connected to said distal catheter shaft section at a location spaced distally from the distal end of said transition tube, said distal catheter shaft section having at least one second inflation hole through the wall thereof intermediate the ends of said balloon, such that said lumen of said transition tube is in fluid communication with said balloon through said first inflation hole, said lumen of said distal catheter shaft section and said second inflation hole.

9. The intravascular catheter assembly of claim 8, further comprising a core member disposed within said lumen of said proximal tubular member and said lumen of said transition tube over at least a portion of the length thereof.

10. The intravascular catheter assembly of claim 9, wherein said core member extends from the distal end of said proximal tubular member distally to a point proximate said radial port.

11. The intravascular catheter assembly of claim 8, further comprising a first and a second active seal means for limiting the egress of inflation fluid, said first active seal means disposed within said lumen of said distal catheter shaft section between said radial port and said first inflation hole and said second active seal means disposed within lumen of said distal catheter shaft section between the distal end thereof and said second inflation hole.

12. The intravascular catheter assembly of claim 11, wherein each of said active seal means includes a section of flexible tubing extending across a gap in the length of said distal catheter shaft section.

13. The intravascular catheter assembly of claim 12, wherein said flexible tubing is manufactured from an elastomeric material.

14. The intravascular catheter assembly of claim 8, further comprising a first and a second passive seal means for limiting the egress of inflation fluid, said first passive seal means disposed within said lumen of said distal catheter shaft section between said radial port and said first inflation hole and said second passive seal means disposed within said lumen of said distal catheter shaft section between the distal end thereof and said second inflation hole.

15. The intravascular catheter assembly of claim 14, wherein said passive seal means include o-rings.

16. An intravascular catheter assembly comprising:
(a) a proximal tubular member having a lumen therethrough;
(b) a transition tube having a proximal end connected to and extending distally from the distal end of said proximal tubular member and having a lumen in fluid communication with said lumen of said proximal tubular member, said transition tube further having a radial port intermediate the length thereof;
(c) a distal catheter shaft section having a proximal end connected to said radial port and a lumen therethrough, said distal catheter shaft section extending distally beyond the distal end of said transition tube, wherein said distal end of said transition tube is sealingly connected to said distal catheter shaft section, said distal catheter shaft section further having at least one first inflation hole through the wall thereof intermediate between said radial port and said distal end of said transition tube;
(d) a balloon having a proximal end and a distal end sealingly connected to said distal catheter shaft section at a location spaced distally from the distal end of said transition tube, said distal catheter shaft section having at least one second inflation hole through the wall thereof intermediate the ends of said balloon, such that said lumen of said transition tube is in fluid communication with said balloon through said first inflation hole, said lumen of said distal catheter shaft section and said second inflation hole;
(e) a first and a second active seal means for limiting the egress of inflation fluid, said first active seal means disposed within said lumen of said distal catheter shaft section between said radial port and said first inflation hole and said second active seal means disposed within said lumen of said distal catheter shaft section between the distal end thereof and said second inflation hole; and,
(f) a first and a second passive seal means for limiting the egress of inflation fluid, said first passive seal means disposed within said lumen of said distal catheter shaft section between said radial port and said first inflation hole and said second passive seal means disposed within said lumen of said distal catheter shaft section between the distal end thereof and said second inflation hole.

17. The intravascular catheter assembly of claim 16, further comprising a core member disposed within said lumen of said proximal tubular member and said lumen of said transition tube over at least a portion of the length thereof.

18. The intravascular catheter assembly of claim 17, wherein said core member extends from the distal end of said proximal tubular member distally to a point proximate said radial port.

19. The intravascular catheter assembly of claim 16, wherein each of said active seal means includes a section of flexible tubing extending across a gap in the length of said distal catheter shaft section.

20. The intravascular catheter assembly of claim 19, wherein said passive seal means include o-rings.

* * * * *